(12) United States Patent
Freitag et al.

(10) Patent No.: US 7,888,534 B2
(45) Date of Patent: *Feb. 15, 2011

(54) DIARYL ALKYLPHOSPHONATES AND METHODS FOR PREPARING SAME

(75) Inventors: Dieter Freitag, Chelmsford, MA (US); Savvas Hadjikyriacou, Chelmsford, MA (US)

(73) Assignee: FRX Polymers, Inc., Chelmsford, MA (US)

( * ) Notice: Subject to any disclaimer, the term of this patent is extended or adjusted under 35 U.S.C. 154(b) by 698 days.

This patent is subject to a terminal disclaimer.

(21) Appl. No.: 11/550,158

(22) Filed: Oct. 17, 2006

(65) Prior Publication Data

US 2007/0203355 A1    Aug. 30, 2007

Related U.S. Application Data

(60) Provisional application No. 60/727,680, filed on Oct. 18, 2005, provisional application No. 60/727,619, filed on Oct. 18, 2005.

(51) Int. Cl.
*C07F 9/28* (2006.01)
(52) U.S. Cl. .................................................. 568/14
(58) Field of Classification Search .................. 568/14
See application file for complete search history.

(56) References Cited

U.S. PATENT DOCUMENTS

| | | | |
|---|---|---|---|
| 2,534,242 A | 11/1949 | Cusic | |
| 2,682,522 A | 6/1954 | Coover, Jr. et al. | |
| 2,716,101 A | 8/1955 | Coover, Jr. et al. | |
| 3,153,008 A | 10/1964 | Fox | |
| 3,271,329 A | 9/1966 | Coover, Jr. et al. | |
| 3,326,852 A | 6/1967 | Thomas | |
| 3,442,854 A | 5/1969 | Curtius et al. | |
| 3,932,351 A | 1/1976 | King | |
| 3,932,566 A | 1/1976 | Reader | |
| 3,952,072 A | 4/1976 | Yonemitsu et al. | |
| 4,033,927 A | 7/1977 | Borman | |
| 4,048,106 A | 9/1977 | Hermans | |
| 4,064,107 A | 12/1977 | Stackman et al. | |
| 4,078,016 A | 3/1978 | Kramer | |
| 4,093,582 A | 6/1978 | Mark et al. | |
| 4,152,373 A | 5/1979 | Honig | |
| 4,223,104 A | 9/1980 | Kim et al. | |
| 4,254,177 A | 3/1981 | Fulmer | |
| 4,322,520 A | 3/1982 | Schmidt et al. | |
| 4,328,174 A | 5/1982 | Schmidt et al. | |
| 4,331,614 A | 5/1982 | Schmidt et al. | |
| 4,332,921 A | 6/1982 | Schmidt et al. | |
| 4,374,971 A | 2/1983 | Schmidt et al. | |
| 4,377,537 A * | 3/1983 | Block et al. ................. | 558/122 |
| 4,401,802 A | 8/1983 | Schmidt et al. | |
| 4,408,033 A | 10/1983 | Hefner, Jr. | |
| 4,415,719 A | 11/1983 | Schmidt et al. | |
| 4,474,937 A | 10/1984 | Bales | |
| 4,481,350 A | 11/1984 | Schmidt et al. | |
| 4,508,890 A | 4/1985 | Schmidt et al. | |
| 4,594,404 A | 6/1986 | Kawakami et al. | |
| 4,642,366 A | 2/1987 | Honig et al. | |
| 4,719,279 A | 1/1988 | Kauth et al. | |
| 4,736,052 A | 4/1988 | Nunan et al. | |
| 4,762,905 A | 8/1988 | Schmidt et al. | |
| 4,782,123 A | 11/1988 | Kauth et al. | |
| 5,003,029 A | 3/1991 | Ueda et al. | |
| 5,034,056 A | 7/1991 | VonBonin | |
| 5,039,775 A | 8/1991 | Oyaizu | |
| 5,086,153 A | 2/1992 | Oyaizu | |
| 5,216,113 A | 6/1993 | Schulz-Schlitte et al. | |
| 5,319,058 A | 6/1994 | Hattori et al. | |
| 5,334,692 A | 8/1994 | Hess et al. | |
| 5,525,681 A | 6/1996 | Barron et al. | |
| 5,639,800 A | 6/1997 | VonBonin et al. | |
| 5,719,200 A | 2/1998 | Staendeke et al. | |
| 5,919,844 A | 7/1999 | Shimizu et al. | |
| 6,066,700 A | 5/2000 | Konig et al. | |
| 6,291,630 B1 | 9/2001 | Konig et al. | |
| 6,861,499 B2 | 3/2005 | Vinciguerra | |
| 2004/0167284 A1 | 8/2004 | Vinciguerra et al. | |
| 2005/0020800 A1 | 1/2005 | Levchik et al. | |
| 2005/0222370 A1 | 10/2005 | Freitag et al. | |
| 2006/0020104 A1 | 1/2006 | Freitag | |
| 2007/0203355 A1 | 8/2007 | Freitag et al. | |

FOREIGN PATENT DOCUMENTS

| | | |
|---|---|---|
| DE | 2747554 A1 | 4/1979 |
| DE | 4302958 C1 | 3/1994 |
| EP | 0034239 A1 | 8/1981 |

(Continued)

OTHER PUBLICATIONS

Yao et al., A concise method for the synthesis of diaryl aryl- or alkylphosphonates, 2005. Tetrahedron Lett. 47(22):277-281.

Hudson et al., Some New Observations on an Old Reaction: Disproportionation and the Formation of P-O-P Intermediates in the Michaelis-Arbuzov Reaction of Triaryl Phosphites With Alkyl Halides, May 21, 2004, ARKIVOC, 2004(ix):19-33.

Vasu et al., Synthesis and Fungicidal Activity of Diaryl Methylphosphonates, 1983, Agricultural and Biological Chemistry, 47(11):2657-2659.

Schmidt et al., Aromatische Polyphosphonate: Thermoplastische Polymere von extremer Brandwidrigeit, 1985, Die Angewandte Makromolekulare Chemie, 132(2165):1-8.

(Continued)

*Primary Examiner*—Robert Havlin
(74) *Attorney, Agent, or Firm*—Pepper Hamilton LLP

(57) ABSTRACT

A method for preparing substantially pure optionally substituted diaryl alkylphosphonates from an optionally substituted triarylphosphite and an optionally substituted trialkylphosphite or an optionally substituted alkanol under special reaction conditions is described.

24 Claims, No Drawings

FOREIGN PATENT DOCUMENTS

| | | |
|---|---|---|
| EP | 0077493 B1 | 3/1987 |
| GB | 2043083 | 1/1980 |
| WO | WO 03/029258 A1 | 4/2003 |
| WO | WO 2004/076536 | 9/2004 |
| WO | WO 2004/076537 | 9/2004 |

OTHER PUBLICATIONS

Billmeyer, Textbook of Polymer Science, $2^{nd}$ ed., Wiley Interscience, New York, 1971, pp. 45-52.

Legrand et al., eds., Handbook of Polycarbonates, Marcel Dekker, Inc., New York, 2000 (TOC).

Levchik et al., Overview of Recent Developments in the Flame Retardancy of Polycarbonates, Polymer International, 54(7):981-998, (2005).

Cotter et al., Engineering Plastics: A Handbook of Polyarylethers, Science Publ. S.A., Switzerland 1995 (TOC).

Groggins, Unit Processes in Organic Synthesis, $4^{th}$ ed., McGraw Hill Book Co., 1952, pp. 616-620.

Morgan, Condensation Polymers, Wiley Interscience, New York, 1965, pp. 217-223.

Hudson, H. R. et al, Ouasiphosphonium intermediates. I. Preparation, structure, and nuclear magnetic resonance spectroscopy of triphenyl and trineopentyl phosphite-alkyl halide adducts. *J. Chem. Soc., Perkin Trans.* 1, (1974), pp. 982-985.

Landauer S. R. et al, The Organic Chemistry Of Phosphorus. Part I. Some New Methods For The Preparation Of Alkyl Halides, *J. Chem. Soc*, (1953) pp. 2224-2234.

Phillips, D. I. et al, Rates of Ionization of Phosphoranes, J. Am. Chem. Soc., Jan. 7, 1976, 98(1), pp. 184-189.

Honig, M. L. et al, "A Convenient Synthesis Of Diaryl Methylphosphonates And Transesterificalion Products Therefrom", J. Org. Chem., (1997) 42(2), pp. 379-381.

\* cited by examiner

DIARYL ALKYLPHOSPHONATES AND METHODS FOR PREPARING SAME

CROSS REFERENCE

This application claims priority from U.S. Provisional Application No. 60/727,680 entitled "Method for Preparing High Purity Diaromatic Alkylphosphonates" filed Oct. 18, 2005 and U.S. Provisional Application No. 60/727,619 entitled "Method for Preparing High Purity Diaromatic Alkylphosphonates" filed Oct. 18, 2005, the contents of which are incorporated herein by reference in their entirety.

BACKGROUND

Various methods for the synthesis of diaromatic alkylphosphonates are known. Methods for making diaromatic alkylphosphonates are described in U.S. Pat. Nos. 4,152,373 and 4,377,537, for example. In U.S. Pat. No. 4,152,373, diaromatic alkylphosphonates are prepared by the reaction of a triaromaticphosphite specifically triphenylphosphite and methanol in the presence of a catalytic amount of methyl iodide. The reaction temperatures are higher than the boiling point of methanol (~65° C.), and consequently require a relatively slow addition of methanol in order to keep it from boiling out of the reactor. In this reaction, phenol is a by-product that is distilled from the product in a separate step.

U.S. Pat. No. 4,377,537 describes a method of synthesizing diaromatic methylphosphonates by the reaction of a triarylphosphite (specifically triphenylphosphite) and trialkylphosphite (specifically trimethylphosphite) in the process of a catalytic amount of methyl iodide. The reaction typically involves heating the components to a final temperature of about 230° C. for up to 1 hour. Exothermic reactions for this process occur in two temperature regions, the first around 100° C., and the second near 210° C. Due to the exothermic (even explosive) nature of these reactions when used in a batch process, the reaction scheme described in U.S. Pat. No. 4,377,537 is limited to small scale production of diaromatic alkylphosphonates.

Although some diaromatic alkylphosphonates (e.g. diphenyl methylphosphonate) (Registry number 7526-26-3) are commercially available, they are relatively expensive.

SUMMARY

Embodiments of the invention described herein include a method for preparing diaryl alkylphosphonate including heating optionally substituted triarylphosphite to a defined reaction temperature, adding a mixture comprising optionally substituted trialkylphosphite in molar excess of from at least about 10% to about 50% in relation to the optionally substituted triarylphosphite and a catalyst to the heated optionally substituted triarylphosphite, or adding a mixture comprising optionally substituted alkanol in a molar excess of from at least about 10% to about 50% in relation to the optionally substituted triarylphosphite and a catalyst to the heated optionally substituted triarylphosphite, reacting the optionally substituted triarylphosphite and optionally substituted trialkylphosphite or optionally substituted alkanol to form optionally substituted diaryl alkylphosphonate, and providing optionally substituted diarylalkylphosphonate containing substantially no triarylphosphite. In some embodiments, the optionally substituted trialkylphosphite, or optionally substituted alkanol, may be from at least 20% to about 40% molar excess in relation to the optionally substituted triarylphosphite, and in others, the optionally substituted trialkylphosphite or optionally substituted alkanol may be in about a 13% molar excess in relation to the optionally substituted triarylphosphite.

In some embodiments, the optionally substituted triarylphosphite may be of general formula (III):

wherein $R_1$ may be of general formula (II):

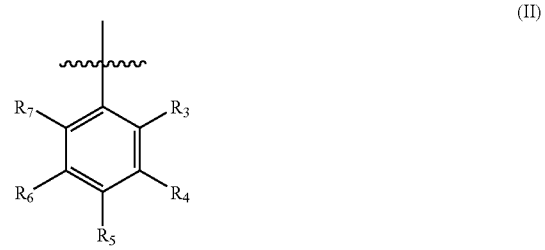

wherein $R_3$, $R_4$, $R_5$, and $R_7$, independently may be selected from hydrogen, trifluoromethyl, nitro, cyano, $C_1$-$C_{20}$ alkyl, an aromatic, a halide, $C_1$-$C_{20}$ alkyl ether, benzyl halide, benzylether, aromatic ether and combinations thereof. In certain embodiments, the optionally substituted triarylphosphite may be triphenylphosphite.

In some embodiments, the optionally substituted trialkylphosphite may be of general formula (IV):

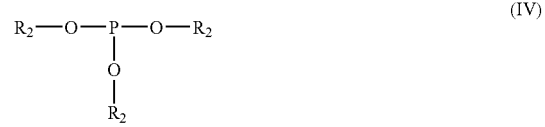

wherein $R_2$ may be a $C_1$-$C_{20}$ alkyl. In certain embodiments, the optionally substituted trialkylphosphite may be trimethylphosphite.

In embodiments, the optionally substituted alkanol may be of general formula (V):

where $R_8$ and $R_9$ may be hydrogen or $C_1$-$C_{20}$ alkyl, and in certain embodiments, the optionally substituted alkanol may be methanol.

In embodiments, the mixture comprising optionally substituted trialkylphosphite or optionally substituted alkanol and the catalyst may be added under a surface of the heated optionally substituted triarylphosphite, and in some embodiments, the optionally substituted trialkylphosphite or optionally substituted alkanol and the catalyst may be added on top of a surface of the heated optionally substituted triarylphosphite.

The catalyst of embodiments may be an alkylating catalyst, and in certain embodiments may be $CH_3I$.

In some embodiments, the defined reaction temperature may be at least greater than the temperature of the highest exotherm of those exotherms created when the reactants are mixed together at room temperature and heated up, and in other embodiments, the defined reaction temperature may be from about 210° C. to about 260° C. In alternative embodiments, the defined reaction temperature may be maintained during the addition of the optionally substituted trialkylphosphite or optionally substituted alkanol and a catalyst.

In embodiments, substantially no toxic by-products may be formed when the optionally substituted diaryl alkylphosphonate prepared using the methods described above are used in subsequent reactions.

Other embodiments of the invention may include methods for preparing optionally substituted diaryl alkylphosphonate including heating optionally substituted triarylphosphite to a reaction temperature at least greater than the highest exotherm, adding a mixture including optionally substituted trialkylphosphite in molar excess of from at least about 10% to about 50% in relation to the optionally substituted triarylphosphite and a catalyst to the heated optionally substituted triarylphosphite, or adding a mixture comprising optionally substituted alkanol in a molar excess of from at least about 10% to about 50% in relation to the optionally substituted triarylphosphite and a catalyst to the heated optionally triarylphosphite, maintaining the reaction temperature during the addition of the optionally substituted trialkylphosphite or optionally substituted alkanol and a catalyst, reacting with the optionally substituted triarylphosphite and optionally substituted trialkylphosphite or optionally substituted alkanol to form optionally substituted diaryl alkylphosphonate, and providing optionally substituted diarylalkylphonsphonate containing substantially no triarylphosphite. In some embodiments, the optionally substituted trialkylphosphite or optionally substituted alkanol may be from at least about 20% to about 40% molar excess in relation to the optionally substituted triarylphosphite, and in others, the optionally substituted trialkylphosphite or optionally substituted alkanol may be in about a 13% molar excess in relation to the optionally substituted triarylphosphite.

In some embodiments, the reaction temperature may be from about 210° C. to about 260° C., and in others, the reaction temperature may be from about 230° C. to about 260° C.

Still other embodiments of the invention include methods for preparing optionally substituted diaryl alkylphosphonate including combining optionally substituted triarylphosphite and at least one catalyst to from a triarylphosphite catalytic mixture, heating the triarylphosphite catalytic mixture, adding at least one optionally substituted trialkylphosphite to the heated triarylphosphite catalytic mixture, or adding at least one optionally substituted alkanol to the heated triarylphosphite catalytic mixture, and reacting the triarylphosphite catalytic mixture and optionally substituted trialkylphosphite or optionally substituted alkanol to form optionally substituted diaryl alkylphosphonate.

In some embodiments, the catalyst may be an alkylating catalyst, and in others, the catalyst may be $CH_3I$. The triarylphosphite catalytic mixture of embodiments may be substantially stable, and may comprise an excess of optionally substituted triarylphosphite in relation to the catalyst. In still other embodiments, reacting using the triarylphosphite catalytic mixture may be carried out at high temperature with substantially no loss of catalyst.

Yet other embodiments of the invention include a catalyst comprising at least one optionally substituted triarylphosphite combined with at least one alkylating catalyst. In certain embodiments, the catalyst may be an alkyl halide of general formula (VII)

$$R_{10}\text{---}X \quad (VII)$$

wherein $R_{10}$ is $C_1$-$C_{20}$ alkyl and X is a halide. In certain embodiments the catalyst may be of general formula (VI)

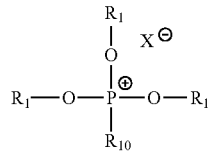

(VI)

wherein $R_1$ is of general formula (II)

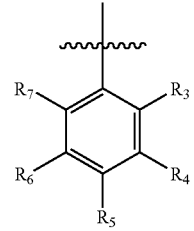

(II)

wherein $R_3$, $R_4$, $R_5$, and $R_7$, independently may be selected from hydrogen, trifluoromethyl, nitro, cyano, $C_1$-$C_{20}$ alkyl, an aromatic, a halide, $C_1$-$C_{20}$ alkyl ether, benzyl halide, benzylether, aromatic ether and combinations thereof, $R_{10}$ is $C_1$-$C_{20}$ alkyl and X is a halide.

DETAILED DESCRIPTION

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring such as but not limited to cyclopentyl, cyclohexyl, methylcyclohexyl and the like. The term "lower alkyl" includes an alkyl group of 1 to 10 carbon atoms.

The term "aryl" or "aryl group" refers to monovalent aromatic hydrocarbon radicals or groups consisting of one or more fused rings in which at least one ring is aromatic in nature. Aryls may include but are not limited to phenyl, napthyl, biphenyl ring systems and the like. The aryl group may be unsubstituted or substituted with a variety of substituents including but not limited to alkyl, alkenyl, halide, benzylic, alkyl or aromatic ether, nitro, cyano and the like and combinations thereof.

"Substituent" refers to a molecular group that replaces a hydrogen in a compound and may include but are not limited to trifluoromethyl, nitro, cyano, $C_1$-$C_{20}$ alkyl, aromatic or aryl, halide (F, Cl, Br, I), $C_1$-$C_{20}$ alkyl ether, benzyl halide, benzyl ether, aromatic or aryl ether, hydroxy, alkoxy, amino, alkylamino (—NHR'), dialkylamino (—NR'R") or other groups which do not interfere with the formation of the diaryl alkylphosphonate.

As defined herein, an "arylol" or an "arylol group" is an aryl group with a hydroxyl, OH, group substituent on the aryl ring. Non-limiting examples of an arylol are phenol, napthalene and the like. A wide variety of arlyols may be used in the embodiments of the invention and are commercially available.

The term "alkanol" or "alkanol group" refers to a compound including an alkyl of 1 to 20 carbon atoms or more having at least one hydroxyl group substituent. Examples of alkanols include but are not limited to methanol, ethanol, 1- and 2-propanol, 1,1-dimethylethanol, hexanol, octanol and the like. Alkanol groups may be optionally substituted with substituents as described above.

The term "alkenol" or "alkenol group" refers to a compound including an alkene 2 to 20 carbon atoms or more having at least one hydroxyl group substituent. The hydroxyl may be arranged in either isomeric configuration (cis or trans). Alkenols may be further substituted with one or more substituents as described above and may be used in place of alkanols in some embodiments of the invention. Alkenols are known to those skilled in the art and many are readily available commercially.

Embodiments of the present invention may include methods for making optionally substituted diaryl alkylphosphonates, optionally substituted diaryl alkylphosphonates prepared using such methods, and compositions related to these methods. The method of some embodiments may include combining optionally substituted triarylphosphite with an at least 10% molar excess of either optionally substituted trialkylphosphite or optionally substituted alkanol and a catalytically effective amount of a catalyst. In embodiments, the optionally substituted triarylphosphite may be heated to a defined reaction temperature prior to the addition of the optionally substituted trialkylphosphite or optionally substituted alkanol and a catalytically effective amount of a catalyst, and this reaction mixture may be reacted to form optionally substituted diaryl alkylphosphonate. In other embodiments, the optionally substituted trialkylphosphite may be combined with a catalytically effective amount of a catalyst and this mixture may be added to optionally substituted triarylphosphite heated to a defined reaction temperature. Without wishing to be bound by theory, combining the components at ambient temperature and heating to a suitable reaction temperature may include an uncontrolled exothermic reaction to occur potentially creating a violent exotherm.

In certain embodiments, optionally substituted diaryl alkylphosphonate may form immediately upon addition to the optionally substituted trialkylphosphite or optionally substituted alkanol and a catalytically effective amount of the catalyst to the heated optionally substituted triarylphosphite. In other embodiments, the heat generated by the reaction may be regulated by the rate at which the optionally substituted trialkylphosphite or optionally substituted alkanol and a catalytically effective amount of the catalyst are added to the heated optionally substituted trialkylphosphite. Therefore, the optionally substituted trialkylphosphite or optionally substituted alkanol and a catalytically effective amount of the catalyst may be added using a controlled method such as, for example, dropping in from above or pumping in from below the surface of the reaction mixture.

In still other embodiments, optionally substituted triarylphosphite and a catalytically effective amount of a catalyst, such as, but not limited to, a methyl halide may be combined to form a stable triarylphosphite catalytic mixture. The triarylphosphite catalytic mixture may be stored following its preparation at ambient temperature for an indefinite period of time, and/or the triarylphosphite catalytic mixture may be heated to a defined reaction temperature and production of optionally substituted diaryl alkylphosphonate may be initiated by the addition of an at least 10% molar excess of optionally substituted alkanol or optionally substituted trialkylphosphite to the heated triarylphosphite catalytic mixture. The triarylphosphite catalytic mixture of embodiments may further contain an excess of optionally substituted triarylphosphite in relation to the catalyst.

Without wishing to be bound by theory when combined with the catalyst, the optionally substituted triarylphosphite may react with the catalyst to form the triarylphosphite catalytic mixture such that substantially no Arbozov reaction occurs, and substantially no exotherm is produced. Moreover, the triarlyphosphite catalytic mixture may substantially increase the boiling point of the catalyst such that the triarylphosphite catalytic mixture may be heated to a temperature greater than 40° C. with substantially no loss of catalytic activity. Therefore, production of optionally substituted diaryl alkylphosphonate may take place at high temperature with substantially no loss of the catalyst due to vaporization of the catalyst as may occur when the catalyst is added with the optionally substituted trialkylphosphite or optionally substituted alkanol or added individually either by dropping into the reaction or pumping in from below the reaction surface.

In certain embodiments, optionally substituted diaryl alkylphosphonate may form immediately upon addition of the optionally substituted trialkylphosphite or optionally substituted alkanol to the heated triarylphosphite catalytic mixture. In other embodiments, the heat generated by the reaction may be regulated by the rate at which the optionally substituted trialkylphosphite or optionally substituted alkanol are added to the heated trialkylphosphite catalytic mixture. Therefore, the optionally substituted trialkylphosphite or optionally substituted alkanol may be added using a controlled method such as, for example, dropping in from above or pumping in from below the surface of the reaction mixture.

In embodiments of the invention, the defined reaction temperature may be at least higher than the highest exotherm when the components are mixed at ambient temperature and heated allowing the reaction to occur, and in certain embodiments, the reaction temperature may be at least greater than the temperature of the highest exotherm and below the temperature at which the optionally substituted diaryl alkylphosphonate produced is thermally degraded. The reaction temperature of embodiments may therefore be from about 210° C. to about 260° C., and in others, the reaction temperature may be from about 230° C. to about 260° C. Without wishing to be bound by theory, the large observed uncontrolled exotherm, when the reactants are combined at room temperature and heated, may be eliminated by performing the reaction at a temperature at least greater than the highest exotherm and the volatility of the reaction mixture may be reduced allowing for the reaction to occur more safely.

The optionally substituted diaryl alkylphosphonates prepared by any of the methods described above may be substantially free of contaminants, such as, for example, residual optionally substituted triarylphosphite which may allow optionally substituted diaryl alkylphosphonates prepared using methods of embodiments of the invention to be used in subsequent condensation reactions with substantially no formation of toxic by-products.

The diaryl alkylphosphonates or optionally substituted diaryl alkylphosphonates of embodiments may be of general formula (I):

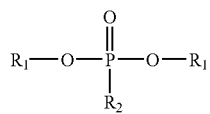

(I)

where $R_2$ may be $C_1$-$C_{20}$ alkyl and $R_1$ may be an aromatic or aryl group, or a substituted aryl group of formula (II):

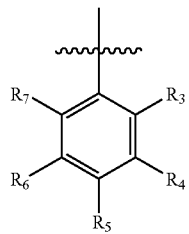

(II)

where $R_3$, $R_4$, $R_5$, and $R_7$ may independently be any substituent including but not limited to hydrogen, $C_1$-$C_{20}$ alkyl, aromatic or aryl group, trifluoromethyl, nitro, cyano, halide (F, Cl, Br, I), $C_1$-$C_{20}$ alkyl ether, benzyl halide, benzyl ether, aromatic or aryl ether, or optionally substituted versions of these and $R_3$, $R_4$, $R_5$, $R_6$, and $R_7$ are essentially unaffected by the reaction. In certain embodiments, the diaryl alkylphosphonate may be diphenyl methylphosphonate.

Optionally substituted triarylphosphite may be of general formula (III):

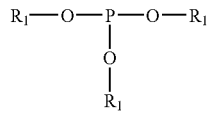

(III)

where $R_1$ may be an aromatic or aryl group, or a substituted aryl group of formula (II), and in some embodiments, the triarylphosphite may be triphenylphosphite.

Optionally substituted trialkylphosphites may be of general formula (IV):

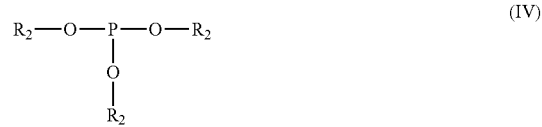

(IV)

where $R_2$ may be $C_1$-$C_{20}$ alkyl, and in some embodiments, the trialkylphosphite may be trimethylphosphite.

Optionally substituted alkanols of embodiments presented herein, may be of general formula (V):

(V)

where $R_8$ and $R_9$ may independently be hydrogen or $C_1$-$C_{20}$ alkyl, and in some embodiments, the optionally substituted alkanol may be methanol.

Various molar ratios of the reactants may be used in embodiments of the invention. In some embodiments, the optionally substituted alkanol or optionally substituted trialkylphosphite may be provided in a molar excess relative to the optionally substituted triarylphosphite. In certain embodiments, the optionally substituted alkanol or optionally substituted trialkylphosphite may be in at least about 50% molar excess relative to the optionally substituted triarylphosphite, and in other embodiments, the optionally substituted alkanol or optionally substituted trialkylphosphite may be at least about 10% molar excess relative to the optionally substituted triarylphosphite. In still other embodiments, the optionally substituted alkanol or optionally substituted trialkylphosphite may be in a molar excess of from at least about 10% to about 50% relative to the optionally substituted triarylphosphite or at least about 20% to about 40% relative to the optionally substituted triarylphosphite. In some embodiments, the optionally substituted alkanol or optionally substituted trialkylphosphite may be in excess relative to the optionally substituted triarylphosphite of about 13%.

In embodiments in which the optionally substituted alkanol or optionally substituted trialkylphosphite may be in molar excess relative to the optionally substituted triarylphosphite, the diaryl alkylphosphonate produced may contain substantially no contaminants such as, for example, residual triarylphosphite. Residual triarylphosphite may be difficult to purify from diaryl alkylphosphonate because the boiling points of the two compounds are similar, and trialkylphosphite may not be distilled away from diaryl alkylphosphonate. Moreover, even a small amount, for example, less than 1% of the total product, of residual triarylphosphite may react with conjugated bisphenols and may be reduced to form toxic phosphines. Additionally, oxidized bisphenol may form colored by-products. In either case, the resulting oligomeric or polyphosphonate may be tainted and unuseable.

In some embodiments, the catalyst may include, but are not limited to, alkyl chlorides, alkyl bromides and alkyl iodides in which the alkyl groups may carry one or more of a variety of substituents. In other embodiments, methyliodide may be the catalyst. Other known alkylating catalysts that may be used in the present invention include, but are not limited to, sulfonic acid esters, sulfuric acid esters, and sultones. Strong acids such as, but not limited to, trifluoromethane sulfonic acid, perfluorobutane sulfonic acid and perfluorooctane sulfonic acid may also serve as catalysts in this reaction. The amount of catalyst added to the reaction may vary among embodiments and may be from about 0.01% to about 10% by weight relative to the triarylphosphite. In other embodiments, the catalyst may be from about 0.5% to about 5% by weight relative to the triarylphosphite.

The method of the present invention is not limited by how a catalyst is added. For example, the catalyst may be combined with the optionally substituted triarylphosphite prior to the addition of the optionally substituted alkanol or optionally substituted alkylphosphite, or the catalyst may be added concurrently with the addition of optionally substituted alkanol or optionally substituted alkylphosphite.

In embodiments, one or more reactant and/or catalysts may be added from above onto the upper surface of the reaction mixture. For example, optionally substituted alkanol, or optionally substituted alkanol and a catalyst, may be added to a reaction mixture containing optionally substituted triarylphosphite or triarylphosphite and a catalyst via an addition funnel. The alkanol or alkanol/catalyst mixture may then be dropped onto the surface of the reaction mixture in a controlled manner. In other embodiments, the optionally substituted alkanol, or optionally substituted alkanol and a catalyst, may be pumped into the reaction mixture thereby adding the alkanol or alkanol/catalyst mixture from below the surface of the reaction mixture. Pumping components into a reaction mixture may allow for a constant stream of optionally substituted trialkylphosphite or optionally substituted alkanol and a catalyst to be provided to heated optionally substituted triarylphosphite or optionally substituted trialkylphosphite. Or, optionally substituted alkanol may be provided to heated triarylphosphite catalytic mixture from below the surface of the reaction mixture in a controlled manner. Without wishing to be bound by theory, adding components such as the optionally substituted alkanol, optionally substituted trialkylphosphite, and/or a catalyst from below the surface of the reaction mixture may allow for improved residence time of that component in the reaction mixture increasing the time in which the reactants may react since the heat evolved during the reaction or the defined reaction temperature may be such that one or more of these components evaporate out of the reaction mixture if added to the surface of the reaction mixture. Adding the reaction components from below may result in improved reaction efficiency, conversion time, and product yield. In other embodiments, the feed rate of the optionally substituted trialkylphosphite or optionally substituted alkanol and a catalyst may be increased by pumping these components beneath the surface of the reaction mixture reducing the reaction time compared to the overhead addition method by as much as by half.

Without wishing to be bound by theory in embodiments in which triarylphosphite is reacted with trialkyl phosphite, the synthesis of diaryl alkylphosphonate may occur as illustrated in scheme (I):

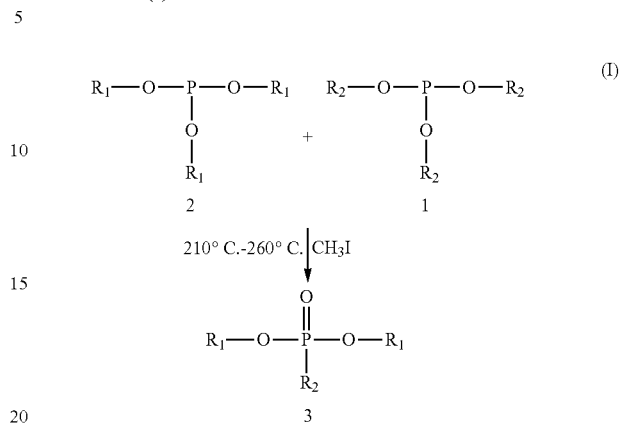

wherein $R_1$ may be an aromatic or aryl group, or a substituted aryl group of formula (II) and $R_2$ may be $C_1$-$C_{20}$ alkyl.

In embodiments in which trarylphosphite is reacted with optionally substituted alkanol, the synthesis of diaryl alkylphosphonate may occur as illustrated in scheme (II):

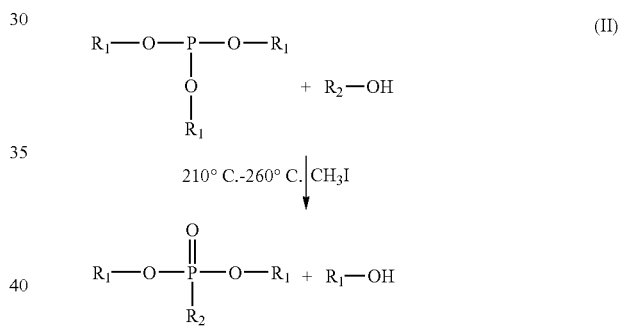

wherein $R_1$ may be an aromatic or aryl group, or a substituted aryl group of formula (II) and $R_2$ may be $C_1$-$C_{20}$ alkyl.

Still other embodiments, a triarylphosphite catalytic mixture, may be formed by combining optionally substituted triarylphosphite with a catalyst such as, for example, a methyl halide catalyst, and heated to a defined reaction temperature before the addition of optionally substituted trialkylphosphite or optionally substituted alkanol. In some embodiments, the optionally substituted triarylphosphite may form a complex with the catalyst without undergoing an Arbozov reaction resulting in a catalyst of general formula (VI):

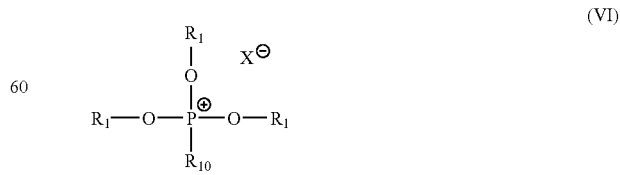

wherein $R_1$ may be an aromatic or aryl group, or a substituted aryl group of formula (II); $R_{10}$ may be hydrogen or $C_1$-$C_{20}$ alkyl; and X may be a halide such as F, Cl, Br, or I. The catalyst of such embodiments may be stable at ambient temperature, or heated to a temperature up to about 260° C. without loss of catalytic activity. The stability of the catalytic complex may be such that the catalyst complex may be stored for an indefinite period of time. The reaction by which the catalyst of embodiments is formed may be reversed at high temperature. Therefore in some embodiments, the catalyst of general formula VI and optionally substituted triarylphosphite may be heated to a defined reaction temperature of at least about 210° C. and optionally substituted alkanol or optionally substituted trialkylphosphite may be added to create a reaction mixture used to prepare optionally substituted diaryl alkyl phosphonate. In such embodiments, diaryl alkylphosphonate may be prepared without providing an additional catalyst.

Advantageously, the diaryl alkylphosphonates produced by embodiments of the invention may be prepared in one-pot, so there may be no need to isolate or purify intermediates. Additionally, by-products such as dialkyl arylphosphite, triarylphosphite, arylols, methoxyaryls, diaryl alkylphosphates, diaryl methylphosphite and residual triarylphosphite may be minimized or eliminated, so one or more separation steps in which by-products are removed may not be necessary. In certain embodiments, triarylphosphite may be avoided as a by-product. The diaryl alkyphosphonates produced by the present invention may, therefore, be easier to purify or produce at a level of purity sufficient for subsequent reactions.

A wide variety of diaromatic alkylphosphonates may be produced using the present invention. These may be used as monomers in the synthesis of polymers, such as, but not limited to, polyphosphonates and copolymers of carbonates and phosphonates. These polymers have exceptional fire resistance and are useful in a wide variety of applications encountered in everyday life.

Having generally described the invention, a more complete understanding thereof may be obtained by reference to the following examples that are provided for purposes of illustration only and do not limit the invention.

oil bath, and the rate of addition were adjusted to maintain the temperature of the reaction mixture between 230-250° C. When the addition was complete the oil bath temperature was set to 245° C. and the reaction mixture was stirred for one additional hour, and subsequently allowed to cool to room temperature. The crude yield was 3060-3080 grams.

The crude product was purified by vacuum distillation through a 12-inch vigreux column. Typically, a forerun of 400-500 grams was taken from 46 to 108° C. (0.03-0.1 mm Hg). The main fraction of 1700-1800 grams was taken from 90 to 104° C. (0.03-0.05) mm Hg) leaving a pot residue of up to 200 grams. Specific details for each example are provided in Table 1 below.

TABLE 1

Summary of Examples 1-4

| Example | Triphenyl-phosphite, g | Trimethyl-phosphite, g | Methyl Iodide, g | Crude Yield, g |
| --- | --- | --- | --- | --- |
| 1 | 2480 | 563.2 | 36.0 | 3071 |
| 2 | 2480 | 563.2 | 36.0 | 3069 |
| 3 | 2480 | 563.2 | 36.0 | 3059 |
| 4 | 2480 | 563.2 | 36.0 | 3069 |

The crude products from each of the examples above (1-4) were analyzed by gas chromatography. Pure standards of each starting material and the product were used to establish retention times. From this analysis, the amount of the desired product, residual starting materials, and any side products were measured. The crude reaction mixture was diluted with acetone and injected into the gas chromatograph. All of the peaks measured were assigned a chemical structure. The results are summarized in Table 2. It is of significance that no triphenylphosphite is present in the crude reaction mixture. As a result, no phosphine compounds can form when this monomer is subsequently used in polymerization reactions with diphenols.

TABLE 2

Summary of Gas Chromatograph Analyses of Examples 1-4

| Example | Triphenylphosphite, % (starting material) | Dimethlphenylphosphite, % (intermediate) | Diphenyl methylphosphonate, % (product) | Phenol, % (by-product) | *Other % |
| --- | --- | --- | --- | --- | --- |
| 1 | 0.0 | 6.98 | 89.2 | 2.2 | 1.62 |
| 2 | 0.0 | 10.91 | 82.95 | 2.77 | 3.37 |
| 3 | 0.0 | 6.83 | 82.01 | 4.50 | 6.66 |
| 4 | 0.0 | 6.23 | 90.65 | 2.54 | 057 |

*Other is comprised of one or more of the following; anisole, trimethylphosphite, diphenylmethylphosphate.

Examples 1-4

All glassware was oven dried overnight at 110° C. and assembled under a nitrogen purge. A 5 liter flask equipped with an overhead stirrer, oil bath, addition funnel, water-cooled condenser with nitrogen by-pass, and thermometer was used as the reaction vessel. The flask was charged with 2480 grams (8 mole) of triphenylphosphite. When the temperature of the triphenylphosphite reached 235° C., a solution of 563.2 grams (4.54 moles) of trimethylphosphite and 36 grams of methyl iodide was added drop wise over a 5-6 hour period. This represents an excess of 13.4% mole of the trimethylphosphite. During the addition, the temperature of the Example 5

Comparative

This example was conducted using the same apparatus and same starting materials as described in Examples 1-4. In this case, stoichiometric quantities of the reactant as were used (i.e., no excess of either reactant). 310 g Triphenylphosphite (1 mol), 62 g triphenylphosphite (0.5 mol), and 2 mls of methyl iodide were charged to the reactor. The reactor was heated to 120° C. and an exothermic reaction caused the temperature to climb to 167° C. The temperature was maintained for 30 minutes and then increased to 215° C. A second exothermic reaction caused the temperature to increase to 240° C. The temperature was maintained for an additional 30 minutes and then allowed to cool.

The crude product was analyzed by gas chromatography as described previously. The results are presented in Table 3. As indicated, the comparative Example 5 that used no excess of the trialkylphosphite contains a significant amount of triphenylphosphite in the crude product.

In an attempt to remove the triphenylphosphite, the crude product was subjected to vacuum distillation through a 12-inch vigreux column. The main fraction from the vacuum distillation process still contained a significant amount of triphenylphosphite. Attempts to remove the remaining triphenylphosphite by vacuum distillation were unsuccessful presumably due to the similarity in boiling points of this compound and the desired product (i.e., diphenyl methylphosphonate).

TABLE 3

Gas Chromatographic Analysis of Comparative Example 5

| Example | Triphenylphosphite, % (starting material) | Dimethlphenylphosphite, % (intermediate) | Diphenyl methylphosphonate, % (product) | Phenol, % (by-product) | *Other % |
|---|---|---|---|---|---|
| 5 | 16.35 | 0.63 | 77.38 | 3.38 | 2.25 |

*Other is comprised of one or more of the following; anisole, trimethylphosphite, diphenylmethylphosphate.

By following the state-of-the-art method for preparing diaromatic alkylphosphonate compounds, it is clear that some starting material (i.e., triphenylphosphite) remains in the crude reaction mixture. This material is practically impossible to remove by vacuum distillation or other known purification techniques. If the diaromatic alkylphosphonate contaminated with triphenylphosphite is used to prepare polymers, for example, with conjugant diphenols, toxic phosphine compound formation is favored. Exposure to these dangerous compounds can occur during subsequent work-up and handling of the polymer or by others that come into contact with this material.

Example 6

All glassware was oven dried overnight at 110° C. and assembled under a nitrogen purge. A 5 liter flask equipped with an overhead stirrer, oil bath, addition funnel, water-cooled condenser with nitrogen by-pass, and thermometer was used as the reaction vessel. The flask was charged with 1552 grams (4.86 mole) of triphenylphosphite, and the oil bath was set to heat to 250° C. When the temperature of the triphenylphosphite reached 250° C., a solution of 176.0 g (5.5 mole, 13% molar excess) of methanol and 5.0 grams of methyl iodide was added drop wise over about a 5 hour period. During the addition, the temperature of the oil bath, and the rate of addition were adjusted to maintain the temperature of the reaction mixture between 230-250° C. When the addition was complete, the oil bath temperature was set to 245° C. and the reaction mixture was stirred for one additional hour and subsequently allowed to cool to room temperature. The crude yield was 1724 grams. The crude product was purified by vacuum distillation through a 12-inch vigreux column.

Example 7

Comparative

All glassware was oven dried overnight at 110° C. and assembled under a nitrogen purge. A 5 liter flask equipped with an overhead stirrer, oil bath, addition funnel, water-cooled condenser with nitrogen by-pass, and thermometer was used as the reaction vessel. The flask was charged with 388 grams (1.25 mole) of triphenylphosphite, and the oil bath was set to heat to 250° C. When the temperature of the triphenylphosphite reached 250° C., a solution of 40.0 g (1.25 mole, 0% molar excess) of methanol and 1.25 grams of methyl iodide was added drop wise over about a 2.25 hour period. During the addition, the temperature of the oil bath and the rate of addition were adjusted to maintain the temperature of the reaction mixture to about 250° C. When the addition was complete, the oil bath temperature was set to 245° C. and the reaction mixture was stirred for one additional hour and subsequently allowed to cool to room temperature. The crude yield was 425 grams.

Prior to purification, the crude products were analyzed by gas chromatography. Pure standards of each starting material and the product were used to establish retention times. From this analysis, the amount of the desired product, residual starting materials and any side products were measured. The results are summarized below in Table 4.

TABLE 4

Gas Chromatographic Analysis of Examples 6-7

| Example | Triphenylphosphite, % (starting material) | Dimethlphenylphosphite, % (intermediate) | Diphenyl methylphosphonate, % (product) | Phenol, % (by-product) | *Other % |
|---|---|---|---|---|---|
| 6 | 0 | 1.2 | 77.30 | 18.5 | 3.0 |
| 7 | 2.91 | 0.48 | 74.80 | 20.65 | 4.07 |

*Other is comprised of one or more of the following; anisole, diphenylmethylphosphate.

As indicated by the results in Table 4, the comparative Example 7 that used no excess of methanol, contains triphenylphosphite in the crude product. Attempts to remove the remaining triphenylphosphite by vacuum distillation were unsuccessful presumably due to the similarity in boiling points of this compound and the desired product (i.e., diphenyl methylphosphonate).

In an attempt to remove the triphenylphosphite, the crude product was subjected to vacuum distillation through a 12-inch vigreux column. The main fraction from the vacuum distillation process still contained a significant amount of triphenylphosphite. Attempts to remove the remaining triphenylphosphite by vacuum distillation were unsuccessful presumably due to the similarity in boiling points of this compound and the desired product (i.e., diphenyl methylphosphonate).

By following the state-of-the-art method for preparing diaromatic alkylphosphonate compounds, it is clear that some starting material (i.e., triphenylphosphite) remains in the crude reaction mixture. This material is practically impossible to remove by vacuum distillation or other known purification techniques. If the diaromatic alkylphosphonate contaminated with triphenylphosphite is used to prepare polymers, for example, with conjugated diphenols, toxic phosphine compound formation is favored. Exposure to these dangerous compounds can occur during subsequent work-up and handling of the polymer or by others that come into contact with this material.

Example 8

All glassware was oven dried overnight at 110° C. and assembled under a nitrogen purge. A 5 liter flask equipped with an overhead stirrer, oil bath, addition funnel, water-cooled condenser with nitrogen by-pass, and thermometer was used as the reaction vessel. The flask was charged with 2560 grams (8.00 mole) of triphenylphosphite and 36.7 grams of iodomethane and were mixed together in the reaction flask at room temperature. During mixing, no exotherm was observed. The mixture was then heated under nitrogen to 240° C. When 240° C. was reached, a solution of 550.0 g (4.3 mole) of trimethylphosphite was added to the mixture from the feeding funnel. Some discoloration was observed during heating, however this disappeared when trimethylphosphite was added. No reflux was observed during either mixing triphenylphosphite and catalyst or heating up this mixture before addition of trimethylphosphite. Addition time was 3 hours during which the reaction was kept under control at from 210° C. to 260° C. After the addition, the temperature of the reaction mixture was held at 240° C. for an additional hour and then cooled to room temperature. The products were then analyzed. Crude yield was 3140 g.

No exothermic activity was detected during the reaction. The mixture of triphenylphosphite and iodomethane obtained a deep red-purple color upon heating. In addition no refluxing of iodomethane could also be observed. Without wishing to be bound by theory, the triphenylphosphite and iodomethane may react to form trisphenoxymethylphosphonium iodide salt.

TABLE 5

Gas Chromatographic Analysis of Example 8

| | Retention time, min. | | | | |
|---|---|---|---|---|---|
| Phenol 9.9 | DMPP(i) 13.6 | P-diester 17.17 | TPP(i) 19.72 | TPP(a) 21.0 | Total |
| Analysis % 0.775 | 6.161 | 72.971 | 0 | 3.975 | 83.882 |
| Normalized % 0.900 | 7.300 | 87.000 | 0 | 4.800 | 100.000 |

TABLE 5-continued

Gas Chromatographic Analysis of Example 8

| | Retention time, min. | | | | |
|---|---|---|---|---|---|
| Phenol 9.9 | DMPP(i) 13.6 | P-diester 17.17 | TPP(i) 19.72 | TPP(a) 21.0 | Total |
| gr, normalized 28.3 | 229.2 | 2731.8 | 0 | 150.7 | 3140.0 |

Theoretically at 100% yield there should be: 248 × 12 = 2976.0 g of P-diester.
Experimental yield: (2731.8 × 100)/2976 g = 91.8%
DMPP(i) = Dimethylphenylphosphite
P-diester = Diphenyl methylphosphonate
TPP(i) = Triphenylphosphite
TPP(a) = Triphenylphosphate

What is claimed is:

1. A method for preparing an optionally substituted diaryl alkylphosphonate comprising:
    heating an optionally substituted triarylphosphite to a temperature of from about 210° C. to about 260° C.;
    adding to the heated optionally substituted triarylphosphite a mixture comprising:
        (i) an optionally substituted trialkylphosphite in a molar excess of from at least 10% to about 50% of the optionally substituted triarylphosphite and further a catalyst; or
        (ii) an optionally substituted alkanol in a molar excess of from at least 10% to about 50% of the optionally substituted triarylphosphite and further a catalyst; and
    reacting the mixture and the heated optionally substituted triarylphosphite to form the optionally substituted diaryl alkylphosphonate wherein the optionally substituted diaryl alkylphosphonate contains less than 1% total product residual triarylphosphite.

2. The method of claim 1, wherein the optionally substituted trialkylphosphite or optionally substituted alkanol is from at least about 20% to about 40% molar excess of the optionally substituted triarylphosphite.

3. The method of claim 1, wherein the optionally substituted trialkylphosphite or optionally substituted alkanol is about 13% molar excess of the optionally substituted triarylphosphite.

4. The method of claim 1, wherein the optionally substituted triarylphosphite is of general formula (III):

(III)

wherein $R_1$ is of general formula (II):

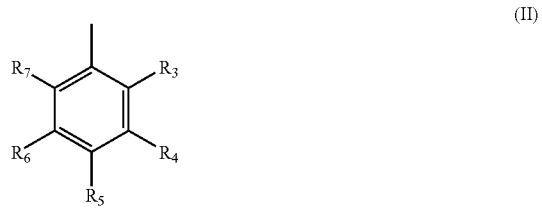

(II)

wherein $R_3$, $R_4$, $R_5$, $R_6$, and $R_7$, independently, are selected from hydrogen, trifluoromethyl, nitro, cyano, $C_1$-$C_{20}$ alkyl, an aromatic, a halide, $C_1$-$C_{20}$ alkyl ether, benzyl halide, benzylether, aromatic ether and combinations thereof.

5. The method of claim 1, wherein the optionally substituted triarylphosphite is triphenolphosphite.

6. The method of claim 1, wherein the optionally substituted trialkyphosphite is of general formula (IV):

(IV)

wherein $R_2$ represents a $C_1$-$C_{20}$ alkyl.

7. The method of claim 1, wherein the optionally substituted trialkylphosphite is trimethylphosphite.

8. The method of claim 1, wherein the optionally substituted alkanol is of general formula (V):

(V)

where $R_8$ and $R_9$ may independently be hydrogen or $C_1$-$C_{20}$ alkyl, and in certain embodiments, the optionally substituted alkanol may be methanol.

9. The method of claim 1, wherein the optionally substituted alkanol is methanol.

10. The method of claim 1, wherein the mixture is added under a surface of the heated optionally substituted triarylphosphite.

11. The method of claim 1, wherein the mixture is added on top of a surface of the heated optionally substituted triarylphosphite.

12. The method of claim 1, wherein the catalyst is an alkylating catalyst.

13. The method of claim 1, wherein the catalyst is $CH_3I$.

14. The method of claim 1, wherein the defined reaction temperature is at least greater than an exotherm created when an optionally substituted triarylphosphite is mixed at room temperature with a catalyst and an optionally substituted trialkylphosphite or an optionally substituted alkanol and further heated.

15. The method of claim 1, further comprising maintaining the defined reaction temperature during the addition of the mixture.

16. The method of claim 1, wherein substantially no toxic by-products are formed when the optionally substituted diaryl alkylphosphonate prepared is used in subsequent reactions.

17. A method for preparing optionally substituted diaryl alkylphosphonate comprising:
combining an optionally substituted triarylphosphite and at least one catalyst to form a triarylphosphite catalytic mixture;
heating the triarylphosphite catalytic mixture to from about 210° C. to about 260° C.;
adding to the heated triarylphosphite catalytic mixture:
(i) an optionally substituted trialkylphosphite in a molar excess of from at least 10% to about 50% of the optionally substituted triarylphosphite; or
(ii) an optionally substituted alkanol in a molar excess of from at least 10% to about 50% of the optionally substituted triarylphosphite; and
reacting the triarylphosphite catalytic mixture and the at least one optionally substituted trialkylphosphite or at least one optionally substituted alkanol to form the optionally substituted diaryl alkylphosphonate wherein the optionally substituted diaryl alkylphosphonate contains less than 1% total product residual triarylphosphite.

18. The method of claim 17, wherein the catalyst is an alkylating catalyst.

19. The method of claim 17, wherein the catalyst is methyl iodide.

20. The method of claim 17, wherein the triarylphosphite catalytic mixture is stored for an indefinite period of time prior to heating.

21. The method of claim 17, wherein the triarylphosphite catalytic mixture is substantially stable at ambient temperature.

22. The method of claim 17, wherein the triarylphosphite catalytic mixture comprises an excess of the optionally substituted triarylphosphite compared to the catalyst.

23. The method of claim 17, wherein the reacting step occurs at high temperature with substantially no loss of catalyst.

24. The method of claim 17, wherein the at least one optionally substituted trialkylphosphite or the at least one optionally substitute alkanol is provided in a molar excess of from at least 10% to about 50% of the optionally substituted triarylphosphite and a catalyst.

* * * * *